(12) United States Patent
Zhu et al.

(10) Patent No.: US 12,109,304 B1
(45) Date of Patent: Oct. 8, 2024

(54) ORAL PATCH FOR TREATING MOUTH ULCERS

(71) Applicant: Xiamen LP Pharmaceutical Co., Ltd., Xiamen (CN)

(72) Inventors: Haijian Zhu, Xiamen (CN); Rongbin Ling, Xiamen (CN); Avinash Singh, Xiamen (CN); Liyan Xie, Xiamen (CN); Xiaojin Xiao, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 18/522,062

(22) Filed: Nov. 28, 2023

(30) Foreign Application Priority Data

Nov. 13, 2023 (CN) .......................... 202311502784.3

(51) Int. Cl.
| | |
|---|---|
| A61K 9/00 | (2006.01) |
| A61K 9/70 | (2006.01) |
| A61K 31/245 | (2006.01) |
| A61K 31/573 | (2006.01) |
| A61K 47/08 | (2006.01) |
| A61K 47/10 | (2017.01) |
| A61K 47/14 | (2017.01) |
| A61K 47/26 | (2006.01) |
| A61K 47/32 | (2006.01) |
| A61K 47/34 | (2017.01) |
| A61K 47/36 | (2006.01) |
| A61K 47/38 | (2006.01) |
| A61K 47/42 | (2017.01) |
| A61K 47/44 | (2017.01) |
| A61P 1/04 | (2006.01) |
| A61P 17/02 | (2006.01) |

(52) U.S. Cl.
CPC ............ *A61K 9/006* (2013.01); *A61K 9/7046* (2013.01); *A61K 9/7053* (2013.01); *A61K 9/7061* (2013.01); *A61K 9/7069* (2013.01); *A61K 31/245* (2013.01); *A61K 31/573* (2013.01); *A61K 47/08* (2013.01); *A61K 47/10* (2013.01); *A61K 47/14* (2013.01); *A61K 47/26* (2013.01); *A61K 47/32* (2013.01); *A61K 47/34* (2013.01); *A61K 47/36* (2013.01); *A61K 47/38* (2013.01); *A61K 47/42* (2013.01); *A61K 47/44* (2013.01); *A61P 1/04* (2018.01); *A61P 17/02* (2018.01)

(58) Field of Classification Search
None
See application file for complete search history.

(56) References Cited

U.S. PATENT DOCUMENTS

| | | | |
|---|---|---|---|
| 5,914,118 A * | 6/1999 | Yamamura | ................ A61P 7/04 424/404 |
| 6,290,984 B1 * | 9/2001 | Tapolsky | ................ A61P 17/00 424/435 |
| 2021/0186859 A1 * | 6/2021 | Xie | ........................ A61K 47/32 |

FOREIGN PATENT DOCUMENTS

CN 116712415 A * 9/2023

OTHER PUBLICATIONS

Altenburg et al ("The Treatment of Chronic Recurrent Oral Aphthous Ulcers", Dtsch Arztebl Int. vol. 111(40), (2014), p. 665-73) (Year: 2014).*
English translation for CN 116712415A (Year: 2023).*
Fernandes, Felipe Pereira et al., Manufacture and Characterization of Mucoadhesive Buccal Films Based on Pectin and Gellan Gum Containing Triamcinolone Acetonide, International Journal of Polymer Science, Jul. 19, 2018, vol. 2018, Article ID 2403802, Hindawi, https://doi.org/10.1155/2018/2403802.

* cited by examiner

*Primary Examiner* — Sin J Lee
(74) *Attorney, Agent, or Firm* — Perkins Coie LLP; Viola T. Kung

(57) ABSTRACT

The present invention provides an oral patch for localized treatment of mouth ulcers containing combination of tetracaine and triamcinolone as active drugs. The patch is a bilayer structure containing a drug layer with amorphous tetracaine hydrochloride and amorphous triamcinolone acetonide and a water-soluble backing layer without a drug. The oral patch with combination of drugs has improved efficacy over each individual drug. The drug layer comprises 3-20% by weight of amorphous tetracaine hydrochloride, or a pharmaceutical acceptable salt thereof, 0.1-2.0% by weight of amorphous triamcinolone acetonide or a pharmaceutical acceptable salt thereof, 20-95% by weight of a first film-forming material, 1-12% by weight of an adhesive, 1-20% by weight of one or more cooling agent, and optionally 1-12% by weight of a plasticizer. The backing layer comprises 70-95% by weight of one or more film-forming agents, 2-10% by weight of a plasticizer and optionally 1-8% by weight of a flavoring agent.

17 Claims, No Drawings

ORAL PATCH FOR TREATING MOUTH ULCERS

This application claims the priority of Chinese Application No. 202311502784.3, filed Nov. 13, 2023; which is incorporated herein by reference in its entirety.

FIELD OF INVENTION

The present invention relates to invention of oral patches for the local or topical treatment of mouth ulcers.

BACKGROUND OF THE INVENTION

An oral ulcer is a sore that appears anywhere the mouth, which is a common complaint of patients attending outpatient clinics. Aphthous ulcers or canker sores are very common oral mucosal lesions; Oral ulcers are characterized by a loss of the mucosal layer within the mouth. This loss may be acute or chronic, localized or diffuse. An oral ulcer is one of the most common oral problems presenting in primary care and can arise as a result of a number of disorders. Some of these relate to problems around the oropharynx but there is a wide variety of systemic disorders that can also give rise to these lesions. The principal causes of oral ulceration are trauma, recurrent aphthous stomatitis, microbial infections, mucocutaneous disease, systemic disorders, squamous cell carcinoma, and drug therapy.

Oral mucosal ulceration involves a breach in the epithelial covering of mucosa exposing the underlying lamina propria while erosions represent an incomplete breach of the epithelial covering and appears as erythematous patches. Lesions are often debilitating, hampering nutrition, and affecting quality of life.

Widely used treatment for localized pain relief of mouth ulcers are rinse formulation and gel formulation. Rinse formulations are mouthwash with antiseptics. Gel formulations are ointments for oral use containing active drugs. However, due to the short residence time of the drug at the site of action, these treatments require multiple doses throughout the day.

Commonly used drugs for treating oral ulcers are benzocaine or amlexanox as an ointment or a gel, benzydamine mouthwash, doxycycline hyclate as capsule or powder. All formulations widely used are in a form of gels, ointments, or mouthwashes, which require frequent administration.

Tetracaine hydrochloride is a local anesthetic used for temporary relief of pain. It is applied on the affected area for fast and temporary relief of pain. Tetracaine hydrochloride currently available in the market in a form of topical cream, nasal spray, or solution; but such form alone is not effective for treating mouth ulcers.

Triamcinolone acetonide is a synthetic corticosteroid used to treat inflammation, swelling, itching in skin conditions such as eczema, dermatitis, allergies, and rash. The drug is also used in arthritis to reduce the pain and inflammatory. Triamcinolone acetonide is currently available on the market in a form of topical cream, suspension, injection, topical lotion, topical ointment, oral tablets, nasal spray, or dental paste.

There exists a need for a pharmaceutical composition for effective treatment of mouth ulcers; the composition should have a long residence time to avoid frequent administration.

DETAILED DESCRIPTION OF THE INVENTION

The present invention provides a pharmaceutical composition suitable for localized administration to treat mouth ulcers. The pharmaceutical composition contains active ingredients of tetracaine and triamcinolone. The pharmaceutical composition is in a form of oral film or oral patch, which provides direct contact with mouth ulcers and a prolonged release of the drugs. The drug-containing oral patch of the present invention adheres to the mucosa of the ulcer lesion and then disintegrates or dissolves by the saliva for an extended period of 2.5-4 hours, and provides localized onset of action to relieve the pain and inflammation. The oral film formulation avoids gastrointestinal degradation and bypasses the liver first pass effect. The oral film overcomes the problem of short drug residence time when administered by mouthwash, ointment, or gels. The present oral film is effective in reducing numbers and size of oral ulcers and erythema levels. The present oral film is effective in reducing the pain caused by oral ulcers.

The present oral patch contains a combination of two drugs: an anesthetic drug of tetracaine and an anti-inflammatory drug of triamcinolone, for treating oral ulcers. Tetracaine relieves the pain and triamcinolone reduces the inflammation or eczema caused by the ulcers. The present oral patch is an extended-release dosage form. The present oral patch directly attaches to the ulcer and releases the drug for an extended time of 2.5-4 hours. The extended release of the drugs avoids frequent administration of the drugs and overcomes the disadvantage of short residence time by gel or mouthwashes administration.

The active ingredients used in the present oral film are tetracaine or its pharmaceutically acceptable salt, and triamcinolone or its pharmaceutically acceptable salt.

"Pharmaceutically acceptable salts," as used herein, are salts that retain the desired biological activity of the parent compound and do not impart undesired toxicological effects. The pharmaceutically acceptable salt of tetracaine for example includes tetracaine hydrochloride and tetracaine-d6 dihydrochloride. The pharmaceutically acceptable salts of triamcinolone for example include triamcinolone acetonide, triamcinolone diacetate, triamcinolone hexaacetonide, and triamcinolone acetonide sodium phosphate. In the present application, unless otherwise specified, the term "tetracaine" is used interchangeably with a pharmaceutically acceptable salt of tetracaine. In the present application, unless otherwise specified, the term "triamcinolone" is used interchangeably with a pharmaceutically acceptable salt of triamcinolone.

Tetracaine, also known as amethocaine, is chemically designated as benzoic acid, 4-(butylamino)-,2-(dimethylamino) ethyl ester, is an ester-type anesthetic and produces local anesthesia by blocking the sodium ion channels involved in the initiation and conduction of neuronal impulses. Tetracaine hydrochloride occurs as a fine, white, crystalline, odorless powder and soluble in water and ethanol.

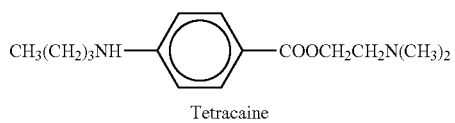

Tetracaine

The chemical name for triamcinolone is (8S,9R,10S,11S,13S,14S,16R,17S)-9-fluoro-11,16,17-trihydroxy-17-(2-hydroxyacetyl)-10,13-dimethyl-6,7,8,11,12,14,15,16-octahydrocyclopenta[a]phenanthren-3-one. Triamcinolone is a corticosteroid with anti-inflammatory and immunomodulating properties. Triamcinolone binds to and activates the glucocorticoid receptor, which leads to activation of anti-inflammatory transcription factors such as lipocortins and inhibition of inflammatory transduction pathways by blocking the release of arachidonic acid and preventing the synthesis of prostaglandins and leukotrienes. Triamcinolone acetonide occurs as a white to almost white, crystalline powder, which has a slight odor and is practically insoluble in water and is very soluble in alcohol.

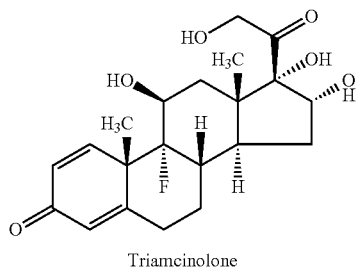

Triamcinolone

Tetracaine is an anesthetic drug. If tetracaine is released in the mouth of a patient, it produces numbness of the tongue in the oral cavity, which causes patient's compliance issue. The oral patch of the present invention is in a bilayer form having a mucoadhesive drug layer comprising tetracaine and triamcinolone, and a backing layer comprising polymers. The backing layer effectively prevents the drug from diffusing to the oral cavity during oral administration and thus preventing numbness of tongue and improving the patient's compliance.

The oral patch of tetracaine and triamcinolone of the present invention is in a bilayer form comprising a drug layer and a backing layer. The drug layer is about 100-250 μm, and the backing layer is about 100-200 μm. The drug layer provides therapeutic effects of anesthesia and anti-inflammation, and the back layer helps the patient compliance by reducing the numbness of the tongue during administration.

The drug layer comprises about 3%-20% by weight of amorphous tetracaine or a pharmaceutically acceptable salt thereof, 0.1%-2.0% by weight of amorphous triamcinolone or a pharmaceutically acceptable salt thereof, about 20-95% by weight of a first film-forming material, about 1-12% by weight of an adhesive, and about 1-20% by weight of a cooling excipient. The backing layer comprises about 70-95% of a second film-forming material, and 2-10% by weight of a plasticizer.

The amount of tetracaine in the drug layer is 0.2-8 mg, preferably 0.5-8 mg, 1-8 mg, 0.5-6 mg, or 1-6 mg. The weight percentage of tetracaine in the drug layer is in general 3-20% w/w. The amount of triamcinolone in the drug layer is 0.01-1.0 mg, preferably 0.02-0.8 mg, 0.02-0.7 mg, 0.03-0.7 mg, or 0.03-0.65 mg. The-weight percentage of triamcinolone in the drug layer is in general 0.1-2.0% w/w.

"About" when used in this application, refers to ±10% of the recited value.

Unless otherwise specified, % used in this application refers to weight by weight %.

The first film-forming materials suitable in the drug layer include one or more materials selected from the group consisting of: hypromellose acetate succinate (HPMCAS), hypromellose (HPMC), ethyl cellulose, acetylated gellan gum, polyvinyl alcohol (PVA), povidone (polyvinylpyrrolidone, PVP), polyethylene glycol, carboxyl methyl cellulose (CMC), hydroxypropyl cellulose (HPC), methylmethacrylate-based copolymer, high amylose starch, and polyethylene Oxide (PEO). Preferred first film-forming materials include HPMCAS, HPMC, ethyl cellulose, acetylated gellan gum, PVA, povidone, polyethylene glycol, and carboxyl methyl cellulose (CMC).

The first film-forming materials have a good compatibility with tetracaine and triamcinolone and they provide the drug layer with a sufficiently high drug-loading capacity. The formed patch has good mechanical properties and flexibility, and the active ingredients tetracaine and triamcinolone are maintained in an amorphous state in the patch without recrystallization or crystal conversion. The weight percentage of the film-forming materials in the drug layer in general is about 20-95% w/w, 30-95% w/w, 20-95% w/w, 25-90% w/w, or 30-90% w/w.

The drug layer includes an adhesive to provides a good adherence of the patch to the mucosa and maximize the efficacy. The localized action of the drugs depends on the adhesion of the patch to the ulcer site for 2.5-4 hours for an extended action. If the oral patch does not adhere properly and the patch moves from the affected site, the efficacy of the oral patch is decreased. Adhesives suitable for the present invention include one or more materials such as polyacrylic acid, sodium alginate, copolymer of ethyl acrylate methyl methacrylate, guar gum, sodium carboxyl methyl cellulose, 5-methyl pyrrolidone chitosan, polyglutamic acid, polycarbophil, dextran sulfate. Preferred adhesives are polyacrylic acid, sodium alginate, copolymer of ethyl acrylate and methyl methacrylate, guar gum, sodium carboxyl methyl cellulose. The amount of adhesive in the oral patch is 1-12% by weight; preferably 1-8% by weight.

Most form of the mouth ulcers have a burning sensation. The present oral patch includes one or more cooling agents in the drug layer to diminish the initial burning and patient discomfort during administration of the path. The cooling agents include one or more excipients of camphor, menthol, mint oil, clove oil, menthyl acetate, xylitol, sorbitol, thymol, and peppermint oil. The cooling agents used in the patch are about 1-20% w/w, preferably 1-18%, w/w or 1-15% w/w.

In one embodiment, the patch further contains one or more plasticizers in the drug layer to improve the folding endurance and manufacturing processability. A suitable plasticizer in the drug layer includes polyethylene glycol (PEG), glycerin, polysorbate, polyethylene glycol, propylene glycol, hexylene glycol and polypropylene glycol, or triethyl citrate. The amount of plasticizer in drug layer is 1-15% by weight, preferably 1-12% by weight.

The backing layer is water-soluble. The backing layer prevents tetracaine and triamcinolone from diffusing into the oral cavity of a patient during oral administration of the patch, and prevents the numbness caused by anesthetic tetracaine hydrochloride.

The second film-forming materials useful in the backing layer include one or more materials selected from the group of: HPMC, HPC, hydroxyethyl cellulose (HEC), hydroxypropylated high amylose starch, methylmethacrylate-based copolymer, povidone, collagen, gelatin, pectin, cellulose acetate phthalate (CAP), polyvinyl alcohol (PVA), and polyvinyl alcohol phthalate (PVAP). Preferred film forming materials are HPMC, HPC, HEC, hydroxypropylated high amylose starch, methylmethacrylate-based copolymer, and povidone. These film-forming materials provide a good barrier effect, which effectively prevent drugs from diffusing out of the drug layer into the oral cavity. The amount of film-forming materials in the backing layer is 70-95%.

The backing layer further contains one or more plasticizers to improve the folding endurance and manufacturing processability of the oral patch. A suitable plasticizer includes polyethylene glycol (PEG), glycerin, polysorbate, polyethylene glycol, propylene glycol, hexylene glycol and polypropylene glycol, or triethyl citrate. The amount of plasticizer in backing layer is 2-10% by weight.

When the thickness of the backing layer is 100 μm to 200 μm, the numbness caused by the tetracaine hydrochloride is significantly reduced. When the thickness of the backing layer is <100 μm, a patient observes the numbness of the tongue and no sense of taste. When the thickness of the backing layer is >200 μm, the release rate of the drugs is slow. A preferred thickness of the backing layer is 100-200 μm.

In one embodiment, one or more flavoring agents can be added to the drug layer and/or the backing layer to improve the taste of the oral patch and to improve the patient compliance. Flavoring agents provide flavor and/or sweetness. Flavoring agents suitable for the drug layer and backing layer include, but are not limited to, aspartame, sucrose, glucose, fructose, xylitol, *stevia*, sucralose, neotame, sodium saccharin, acesulfame, peppermint oil, menthol, orange flavor, pineapple flavor, cherry flavor, apple flavor essence, banana flavor essence, blueberry flavor essence, peach flavor essence, mango flavor essence, and grape flavor essence. The amount of one or more flavoring agents is about 0.5-15%, preferably about 1-8% w/w in the drug layer and in the backing layer.

One or more coloring agents such as titanium dioxide, FD&C colors, D&C colors, and combinations thereof, may be added into the drug layer and/or the backing layer.

The oral patch of the present invention is flexible and elastic to provide comfort to a patient. The oral patch is strong enough to resist breakage caused by movements of the mouth. The administration process is to apply the drug layer side of the patch to the ulcer wound, to cover the ulcer and attach to the mucosa properly.

The present invention provides a tetracaine and triamcinolone patch for treating mouth ulcers. After administration, the drugs directly come in contact with the ulcer. The drugs in general are released about 25-50% in the first hour, about 51-70% in 1.5 hours, and more than 80% after 2.5 hours. The drugs present in the oral patch releases slowly for an extended time of 3-4 hours and provide long term, effective localized treatment.

Tetracaine is a local anesthetic, which reduces the pain within few minutes. Triamcinolone is an anti-inflammatory drug, which reduces pain, inflammation, erythema, and exudate level. Combining both drugs provides a fast and effective treatment. The oral patch has a uniform appearance, thickness, and color, and has good drug stability. The drugs are administered directly on the ulcer for localized treatment, which avoids the first pass metabolism of the drugs and improves efficacy of treatment. The present oral patch provides a direct contact with the oral mucosa and provides a prolonged release of the drugs, reducing the need for administration of repeated doses.

The present invention further provides a method for preparing tetracaine and triamcinolone oral patch. The method comprises the following steps: (a) mixing tetracaine or its pharmaceutically acceptable salt and triamcinolone or its pharmaceutically acceptable salt, one or more first film-forming materials, one or more adhesives, and one or more cooling excipients in a first solvent, to form a clear drug layer solution; (b) coating and drying the drug layer solution on a substrate to form the drug layer; (c) mixing one or more second film-forming materials and one or more plasticizers in a second solvent to form a backing layer solution; (d) coating and drying the backing layer solution on the drug layer to form a bilayer patch on the substrate; and (e) removing the bilayer patch from the substrate to form the oral patch of tetracaine and triamcinolone.

In step (a), the first solvent comprises 20-100% w/w of an organic solvent in water. The organic solvent is selected from the group consisting of: ethanol, dimethyl sulfoxide, dimethyl formamide, and any combination thereof. Preferable organic solvents include ethanol.

In step (b), the second solvent comprises ethanol, water, or any combination thereof. In one embodiment, the second solvent is water.

In steps (a) and (b), all the materials are dissolved completely and form a homogeneous solution, and this results in tetracaine hydrochloride and triamcinolone acetonide in an amorphous form in the oral patch.

In step (b) and (d), the drying temperature is about 40°-100° C., preferably about 60-90° C.

The substrate for forming the bilayer patch includes polyethylene terephthalate, polypropylene resins, and polymethylpentene resins.

After step (e), the bilayer patch is optionally cut into a suitable size and shape, and then further wrapped or packaged.

The oral patch of the present invention has a length of about 1-2 cm, and a width about 1-2 cm; preferably a length of about 1-1.5 cm, and width about 1-1.5 cm; and more preferably length of about 1 cm, and width about 1 cm.

The present invention also provides a method for administering oral patch to a subject for localized treatment of mouth ulcer. The method comprises identifying a subject in need thereof, and attaching the patch onto the mucosa of the ulcer of subject.

The present oral patch is useful in treating a subject that is a mammal, such as humans, horses, dogs, and cats. The present invention is particularly useful in treating humans.

The following examples further illustrate the present invention. These examples are intended merely to be illustrative of the present invention and are not to be construed as being limiting.

EXAMPLES

Example 1: Single Layer Patch (Amorphous Patch)

In this example, tetracaine hydrochloride and triamcinolone acetonide oral patch were prepared according to the formulation and process below. Tetracaine HCl was obtained from Beijing yanjing pharmaceutical co., ltd. Triamcinolone acetonide was obtained from Tianjin Jinhui pharmaceutical group co., ltd.

Formula:
  Tetracaine hydrochloride 2.00 mg (10.00% w/w)
  Triamcinolone acetonide 0.30 mg (1.50% w/w)
  Hypromellose acetate succinate (HPMCAS) 15.53 mg (77.65% w/w)
  Polyvinylpyrrolidone PVP K30 1.50 mg (7.50% w/w)
  Glycerin 0.45 mg (2.25% w/w)
  Sucralose 0.20 mg (1.00% w/w)
  FD&C Yellow No. 6 0.02 mg (0.1% w/w)
  50% Ethanol 90.00 mg (Removed during the process of drying)

Manufacturing Process:
  Dissolve tetracaine hydrochloride and triamcinolone acetonide into solvent with continuous stirring,
  Add other excipients and continue stirring until completely dissolves
  Apply vacuum or stand aside to remove the bubbles, Coat the defoamed film solution in uniform thickness on a substrate, Dry the coating at temperature of about 60° C. to 90° C. to form a patch on the conveyor belt, After the patch was formed, cut the patch into a suitable size, shape and packed in to pouch or in a suitable container.

The oral patch prepared according to the above formula and process had good film property, was easy to tear off from the substrate, smooth appearance and uniform in color. X-ray powder diffraction study shows that tetracaine hydrochloride and triamcinolone acetonide were in amorphous form. In the dissolution test, the release is slow less than 80% drug released in 3 hours.

TABLE 1

Dissolution Test Result of Example 1

| Media | pH 6.8 Phosphate Buffer | | | | | | |
|---|---|---|---|---|---|---|---|
| % Release of Tetracaine Hydrochloride | | | | | | | |
| Time (hour) | 0.50 | 1.00 | 1.50 | 2.0 | 2.50 | 3.00 | 3.5 |
| Dissolved (%) | 15 | 29 | 45 | 60 | 71 | 83 | 90 |

| Media | pH 6.8 Phosphate Buffer | | | | | | |
|---|---|---|---|---|---|---|---|
| % Release of Triamcinolone Acetonide | | | | | | | |
| Time (hour) | 0.50 | 1.00 | 1.50 | 2.0 | 2.50 | 3.00 | 3.5 |
| Dissolved (%) | 10 | 21 | 36 | 52 | 63 | 72 | 86 |

The taste of the patch was good. However, after few seconds of application, anesthetic action of tetracaine hydrochloride affected the tongue, and patients observed tongue numbness.

Example 2: Bilayer Patch (Amorphous Patch)

In this example, bilayer patch was prepared to improve the dissolution of the drug and to avoid the release of drug in oral cavity.

Manufacturing Process:

Dissolve tetracaine hydrochloride and triamcinolone acetonide into first solvent 50% ethanol with continuous stirring Add other excipients and continue stirring until completely dissolves Add backing layer excipient except titanium dioxide into second solvent (water; with continuous stirring, stir until clear solution forms then add titanium dioxide and continue stirring until a homogenous suspension forms.

Apply vacuum or stand aside to remove the bubbles,

Coat the defoamed first drug solution in uniform thickness on a substrate to get drug layer Coat the second backing layer suspension on to the drug layer to get the bilayer patch Coating done at temperature of about 60° C. to 90° C. to form a patch on the conveyor belt, After the patch was formed, cut the patch into a suitable size, shape and packed in to pouch or in a suitable container.

Formulation:

| | Example | 2-1 | 2-2 | 2-3 |
|---|---|---|---|---|
| Drug layer | Tetracaine hydrochloride | 2.00 mg (8.00% w/w) | 2.00 mg (8.00% w/w) | 2.00 mg (8.00% w/w) |
| | Triamcinolone acetonide | 0.30 mg (1.20% w/w) | 0.30 mg (1.20% w/w) | 0.30 mg (1.20% w/w) |
| | HPMCAS | 15.47 mg (61.88% w/w) | 14.47 mg (57.88% w/w) | — |
| | Polyethylene oxide N-80 | — | — | 14.47 mg (57.88% w/w) |
| | HPMC 615 | — | 7.50 mg (30.00% w/w) | 7.50 mg (30.00% w/w) |
| | PVP K30 | 6.50 mg (26.00% w/w) | — | — |
| | Glycerin | 0.45 mg (1.80% w/w) | 0.45 mg (1.80% w/w) | 0.45 mg (1.80% w/w) |
| | Sucralose | 0.25 mg (1.00% w/w) | 0.25 mg (1.00% w/w) | 0.25 mg (1.00% w/w) |
| | FD&C Yellow No. 6 | 0.03 mg (0.12% w/w) | 0.03 mg (0.12% w/w) | 0.03 mg (0.12% w/w) |
| | 50% Ethanol | 90.00 mg | 90.00 mg | 90.00 mg |
| Backing layer | HPMC 615 | 18.10 mg (90.50% w/w) | 18.10 mg (90.50% w/w) | 18.10 mg (90.50% w/w) |
| | Titanium dioxide | 1.00 mg (5.00% w/w) | 1.00 mg (5.00% w/w) | 1.00 mg (5.00% w/w) |
| | Glycerin | 0.50 mg (2.50% w/w) | 0.50 mg (2.50% w/w) | 0.50 mg (2.50% w/w) |
| | Sucralose | 0.40 mg (2.0% w/w) | 0.40 mg (2.0% w/w) | 0.40 mg (2.0% w/w) |
| | Water | 130.00 mg | 130.00 mg | 130.00 mg |

Note:
The solvents used in the manufacturing process removed during the process of drying.

The oral patch prepared had smooth appearance, uniform color. The X-ray powder diffraction study of the patch showed that both the active drugs were in amorphous state. The dissolution experiment example 2-1 and example 2-2 were acceptable showed more than 80% release in 2.5 hours. Example 2-3 had slow and incomplete release at 3.5 hours.

TABLE 2

Dissolution Test Result of Example 2

| Media | pH 6.8 Phosphate Buffer | | | | | | |
|---|---|---|---|---|---|---|---|
| Time (hour) | 0.50 | 1.00 | 1.50 | 2.0 | 2.50 | 3.00 | 3.5 |
| % Release of Tetracaine Hydrochloride | | | | | | | |
| Example 2-1 | 23 | 39 | 61 | 76 | 92 | 100 | 99 |
| Example 2-2 | 31 | 50 | 70 | 90 | 99 | 100 | 100 |
| Example 2-3 | 19 | 31 | 45 | 61 | 70 | 85 | 92 |

| Media | pH 6.8 Phosphate Buffer | | | | | | |
|---|---|---|---|---|---|---|---|
| Time (hour) | 0.50 | 1.00 | 1.50 | 2.0 | 2.50 | 3.00 | 3.5 |
| % Release of Triamcinolone Acetonide | | | | | | | |
| Example 2-1 | 17 | 32 | 50 | 69 | 89 | 97 | 99 |
| Example 2-2 | 25 | 43 | 64 | 85 | 96 | 99 | 100 |
| Example 2-3 | 15 | 25 | 38 | 50 | 64 | 78 | 86 |

Two volunteers suffering from mouth ulcer were selected and a non-clinical study was performed with formulations of Example 2-1 and Example 2-3, to check the drug release in oral cavity and the numbness effect on tongue. The drug layer side was attached to the mucosa of ulcer and the patient was observed for 5 minutes. The volunteers reported an initial burning and slight movement of patch from site of application comparing with the patch of Example 1. The patient with the patch of Example 2-3 showed significant swelling in the mouth after 2 hours. The results show that polyethylene oxide is not suitable as a film-forming material.

In similar experiments, different concentrations of ethanol solution (20% and 100% in water) were prepared as a first solvent; all the physical parameters of patches were satisfactory. The XRD study of oral patch showed the APIs were in amorphous form.

Example 3: Bilayer Patch (Amorphous Patch, Adhesive and Cooling Excipients Added)

In this experiment, adhesive added to improve the patch adhesion to ulcer mucosa and cooling agent added for soothing effect. Manufacturing process is same as described in Example 2.

| | Formulation: | | |
|---|---|---|---|
| | Example | 3-1 | 3-2 |
| Drug layer | Tetracaine hydrochloride | 2.00 mg (6.25% w/w) | 2.00 mg (6.25% w/w) |
| | Triamcinolone acetonide | 0.30 mg (0.94% w/w) | 0.30 mg (0.94% w/w) |
| | Ethyl cellulose | 21.42 mg (66.94% w/w) | 21.42 mg (66.94% w/w) |
| | PVP K30 | 6.00 mg (18.75% w/w) | 6.00 mg (18.75% w/w) |
| | Sodium CMC | 0.96 mg (3.00% w/w) | — |
| | Polyacrylic acid | — | 0.96 mg (3.00% w/w) |
| | Camphor | — | 0.64 mg (2.00% w/w) |
| | Menthol | 0.64 mg (2.00% w/w) | — |
| | Mint oil | 0.16 mg (0.50% w/w) | 0.16 mg (0.50% w/w) |
| | Glycerin | 0.48 mg (1.50% w/w) | 0.48 mg (1.50% w/w) |
| | FD&C Yellow No. 6 | 0.04 mg (0.13% w/w) | 0.04 mg (0.13% w/w) |
| | 50% Ethanol | 100.00 mg | 100.00 mg |
| Backing layer | HPMC 615 | 22.60 mg (90.40% w/w) | 22.60 mg (90.40% w/w) |
| | Titanium dioxide | 1.25 mg (5.00% w/w) | 1.25 mg (5.00% w/w) |
| | Glycerin | 0.65 mg (2.60% w/w) | 0.65 mg (2.60% w/w) |
| | Sucralose | 0.50 mg (2.0% w/w) | 0.50 mg (2.0% w/w) |
| | Water | 145.00 mg | 145.00 mg |

Note:
The solvents used in the manufacturing process removed during the process of drying.

The bilayer patches prepared according to the above formula had smooth appearance, and were uniform in color. The X-ray powder diffraction study of the tetracaine hydrochloride and triamcinolone acetonide oral patch shows that both the drugs were in amorphous state.

Patch size evaluation done by repeating the Example 3-2, cutting the patch into length×width of 1×1, 1×1.5, 1.5×1.5, 2.0×2.0, 2.0×3.0, and 3.0×3.0 cm. The dissolution results showed that the size of the patch with 2.0×3.0 and 3.0×3.0 cm had too faster release of almost 100% release in 2 hours. The patch size from 1×1 to 2.0×2.0 cm showed acceptable results.

The acceptable thickness of the backing layer was determined to be 100-200 μm. When the thickness of the backing layer was less than 100 μm, the drug was released in the oral cavity and tongue numbness observed. When the thickness of the backing layer was more than 200 μm, the release of drug was slow by dissolution study.

TABLE 3

Dissolution Test Result of Example 3

| Media | pH 6.8 Phosphate Buffer | | | | | | |
|---|---|---|---|---|---|---|---|
| Time (hour) | 0.50 | 1.00 | 1.50 | 2.0 | 2.50 | 3.00 | 3.5 |
| % Release of Tetracaine Hydrochloride | | | | | | | |
| Example 3-1 | 25 | 38 | 61 | 75 | 90 | 99 | 100 |
| Example 3-2 | 21 | 37 | 62 | 74 | 89 | 100 | 100 |
| Media | pH 6.8 Phosphate Buffer | | | | | | |
| Time (hour) | 0.50 | 1.00 | 1.50 | 2.0 | 2.50 | 3.00 | 3.5 |
| % Release of Triamcinolone Acetonide | | | | | | | |
| Example 3-1 | 18 | 29 | 52 | 69 | 86 | 97 | 100 |
| Example 3-2 | 16 | 30 | 55 | 70 | 86 | 99 | 100 |

A non-clinical study was performed in 3 volunteers suffering mouth ulcer, it was found the patch attached to the ulcer adequately and there was no drug release in the oral cavity. Volunteers sensed no initial burning and taste of the oral patch was acceptable.

In similar experiments, hypromellose ER grade, carboxyl methyl cellulose and methylmethacrylate-based copolymer were used as film forming release polymer. In all the trials, drugs retained its amorphous form in the patch, with uniform appearance, and extended dissolution of more than 80% in 2.5 hours.

Example 3-2 formulation was repeated for backing layer evaluation. Drug layer formulation was kept constant. In backing layer, same excipients with same weight percentages were used but the total weight of the backing layer was changed from 25 mg to 15 mg, 20 mg, 30 mg, 35 mg, and 40 mg, respectively. The dissolution results showed that backing layer weight ranges from 20-35 mg showed acceptable release rate of more than 80% in 2.5 hours. The dissolution of the tested oral patch with 15 mg backing layer weight was too fast that about 100% was released in 2 hours. The dissolution of the tested oral patch with 40 mg backing layer weight was too slow and about 70% was release in 2.5 hours.

In similar experiments, xylitol, sorbitol along with clove oil were each evaluated as a cooling and taste-modifying agent, all the trials showed acceptable results.

Example 4: Bilayer Patch (Amorphous Patch, Concentration Evaluated)

In these experiments, film forming materials and other excipients concentration were evaluated. Manufacturing process was same as described in Example 2.

| | Formulation: | | |
|---|---|---|---|
| | Example | 4-1 | 4-2 |
| Drug layer | Tetracaine hydrochloride | 2.00 mg (6.25% w/w) | 2.00 mg (6.25% w/w) |
| | Triamcinolone acetonide | 0.3 mg (0.94% w/w) | 0.3 mg (0.94% w/w) |
| | HPMCAS | 16.42 mg (51.31% w/w) | 17.74 mg (55.44% w/w) |
| | PVP K90 | 4.20 mg (13.13% w/w) | |
| | PVP K30 | | 10.00 (31.25% w/w) |
| | Polyacrylic acid | 1.92 mg (6.00% w/w) | 0.32 mg (1.00% w/w) |
| | Camphor | 3.20 mg (10.00% w/w) | 0.32 mg (1.00% w/w) |
| | Mint oil | 0.08 mg (0.25% w/w) | 0.96 mg (3.00% w/w) |
| | Glycerin | 3.84 mg (12.00% w/w) | 0.32 mg (1.00% w/w) |

-continued

| | Formulation: | | |
|---|---|---|---|
| | Example | 4-1 | 4-2 |
| | FD&C Yellow No. 6 | 0.04 mg (0.13% w/w) | 0.04 mg (0.13% w/w) |
| | 50% Ethanol | 100.00 mg | 100.00 mg |
| Backing layer | HPMC 615 | 22.60 mg (90.40% w/w) | 22.60 mg (90.40% w/w) |
| | Titanium dioxide | 1.25 mg (5.00% w/w) | 1.25 mg (5.00% w/w) |
| | Glycerin | 0.65 mg (2.60% w/w) | 0.65 mg (2.60% w/w) |
| | Sucralose | 0.50 mg (2.0% w/w) | 0.50 mg (2.0% w/w) |
| | Water | 145.00 mg | 145.00 mg |

Note:
The solvents used in the manufacturing process removed during the process of drying.

The bilayer patch prepared according to the above formula had a smooth appearance, uniform color with all acceptable qualities.

In similar experiments, different concentrations of glycerin 2%, 5%, 10%, 15% by weight in backing layer tested. The patch with 15% by weight was very soft, and was difficult to dry.

Example 5: Triamcinolone Acetonide Patch (Single Drug)

In this experiment, triamcinolone acetonide patch (single drug) was prepared. The manufacturing process was similar to example 2, except 80% ethanol used in this example for drug layer preparation.

| | Formulation: | |
|---|---|---|
| | Example | 5 |
| Drug layer | Triamcinolone acetonide | 0.30 mg (1.20% w/w) |
| | Ethyl cellulose | 16.95 mg (67.80% w/w) |
| | PVP K30 | 6.00 mg (24.00% w/w) |
| | Sodium alginate | 0.75 mg (3.00% w/w) |
| | Camphor | 0.50 mg (2.00% w/w) |
| | Mint oil | 0.13 mg (0.52% w/w) |
| | Glycerin | 0.37 mg (1.48% w/w) |
| | 80% Ethanol | 100.00 mg |
| Backing layer | HPMC 615 | 22.60 mg (90.40% w/w) |
| | Titanium dioxide | 1.25 mg (5.00% w/w) |
| | Glycerin | 0.65 mg (2.60% w/w) |
| | Sucralose | 0.50 mg (2.0% w/w) |
| | Water | 145.00 mg |

Note:
The solvents used in the manufacturing process removed during the process of drying.

The patch prepared according to the above formula had a smooth appearance, uniform color with all acceptable qualities. The dissolution experiment showed that more than 80% of drug released in 2.5 hours. The patches of Example 4 were used in clinical study. See Example 8 for the experimental results.

Example 6: Tetracaine Hydrochloride Patch (Single Drug)

In this experiment, tetracaine hydrochloride patch (single drug) was prepared. The manufacturing process was similar to example 2, except 20% ethanol used in this example for drug layer preparation.

| | Formulation | |
|---|---|---|
| | Example | 6 |
| Drug layer | Tetracaine hydrochloride | 2.00 mg (8.00% w/w) |
| | Ethyl cellulose | 16.25 mg (65.00% w/w) |
| | PVP K30 | 5.00 mg (20.00% w/w) |
| | Sodium alginate | 0.75 mg (3.00% w/w) |
| | Camphor | 0.50 mg (2.00% w/w) |
| | Mint oil | 0.13 mg (0.52% w/w) |
| | Glycerin | 0.37 mg (1.48% w/w) |
| | 20% Ethanol | 100.00 mg |
| Backing layer | HPMC 615 | 22.60 mg (90.40% w/w) |
| | Titanium dioxide | 1.25 mg (5.00% w/w) |
| | Glycerin | 0.65 mg (2.60% w/w) |
| | Sucralose | 0.50 mg (2.0% w/w) |
| | Water | 145.00 mg |

Note:
The solvents used in the manufacturing process removed during the process of drying.

The patch prepared according to the above formula had a smooth appearance, uniform color and acceptable qualities. The dissolution experiment showed that more than 80% of drug released in 2.5 hours. The patches of Example 5 were used in clinical study. See Example 8 for 5 the experimental results.

Example 7: Tetracaine Hydrochloride and Triamcinolone Acetonide Bilayer Patch

In these examples, Tetracaine hydrochloride and Triamcinolone acetonide used in different strengths. The manufacturing process is similar to example 2. The formulation details are given below.

| | Example | 7-1 | 7-2 | 7-3 |
|---|---|---|---|---|
| Drug layer | Tetracaine hydrochloride | 3.00 mg (9.38% w/w) | 2.00 mg (6.25% w/w) | 1.00 mg (3.13% w/w) |
| | Triamcinolone acetonide | 0.10 mg (0.31% w/w) | 0.20 mg (0.63% w/w) | 0.30 mg (0.94% w/w) |
| | HPMCAS | 20.62 mg (64.44% w/w) | 21.02 mg (65.69% w/w) | 19.92 mg (68.50% w/w) |
| | HPC | | 6.5 mg (20.31% w/w) | 6.5 mg (20.31% w/w) |
| | PEG8000 | 6.00 mg (18.75% w/w) | — | — |
| | Polyacrylic acid | 0.96 mg (3.00% w/w) | 0.96 mg (3.00% w/w) | 0.96 mg (3.00% w/w) |
| | Camphor | 0.64 mg (2.00% w/w) | 0.64 mg (2.00% w/w) | 0.64 mg (2.00% w/w) |
| | Mint oil | 0.16 mg (0.50% w/w) | 0.16 mg (0.50% w/w) | 0.16 mg (0.50% w/w) |
| | Glycerin | 0.48 mg (1.50% w/w) | 0.48 mg (1.50% w/w) | 0.48 mg (1.50% w/w) |
| | FD&C Yellow No. 6 | 0.04 mg (0.13% w/w) | 0.04 mg (0.13% w/w) | 0.04 mg (0.13% w/w) |
| | 50% Ethanol | 100.00 mg | 100.00 mg | 100.00 mg |
| Backing layer | HPMC 615 | 22.60 mg (90.40% w/w) | 22.60 mg (90.40% w/w) | 22.60 mg (90.40% w/w) |
| | Titanium dioxide | 1.25 mg (5.00% w/w) | 1.25 mg (5.00% w/w) | 1.25 mg (5.00% w/w) |
| | propylene glycol | 0.65 mg (2.60% w/w) | 0.65 mg (2.60% w/w) | 0.65 mg (2.60% w/w) |
| | Sucralose | 0.50 mg (2.0% w/w) | 0.50 mg (2.0% w/w) | 0.50 mg (2.0% w/w) |
| | Water | 145.00 mg | 145.00 mg | 145.00 mg |

Note:
The solvents used in the manufacturing process removed during the process of drying.

The dissolution experiment of all batches showed extended release and more than 80% of drug released in 2.5 hours. The patches of all batches were used in clinical study. See Example 8 for the experimental results.

In addition, other different types of backing film forming materials such as hydroxypropyl cellulose (HPC), hydroxyethyl cellulose (HEC), povidone (PVP), hydroxypropylated high amylose starch, hypromellose (HPMC) were evaluated, all the results showed acceptable results.

Example 8: Clinical Study

In this example, clinical study was performed on 30 subjects. A randomized, double-blind, single study performed to evaluate and compare clinical efficacy of Example 5, Example 6, and Example 7-1, 7-2, 7-3 in reducing pain, number and inflammation.

Subjects were divided into 5 groups, each group contained 6 subjects. Subjects selected had a known history of mouth ulcers and had single or multiple ulcers with size less than 10 mm in diameter. A double blinded approach was used where both investigator and patients did not know which treatment was received by each patient. All the parameters were measured by the principal investigator and all the quantitative variables were calculated as mean value.

After enrolment, the size, number of ulcers, pain and erythema were measured by the principal investigator at days 0, 1, 3 and 5. Ulcer size was measured using William's calibrated dental probe and the longest diameter was used as measurement and the pain was evaluated by the subjects based on Visual Analogue Scale before treatment (0 days) and at following days (1, 3 & 5). Erythema level classification is shown as follows,

| Classification | Erythema Level |
|---|---|
| 0 | No erythema |
| 1 | Light red or pink |
| 2 | Red but not dark |
| 3 | Dark red in color |

Patients were instructed not to eat during the treatment process. For each patient, a maximum 3 patches were used. If the patient has two ulcers at same place or with a close distance, a 2.0×2.0 cm patch was used to cover both ulcers. For a single ulcer, a 1.0×1.0 cm patch was used. A patch was gently applied on the ulcer and holded for 3-5 second for a proper adhesion. Results were observed at every 30 minutes interval for 3 hours. Patients were dosed two times a day in the morning and in the evening.

Results: All 30 patients completed the study and gave an overall response rate of 100%. This study showed a reduction in number, size, erythema and pain associated with ulcers in all the tests.

TABLE 4

Comparison of treatment for size of ulcers (mm)

| Group | Mean ulcer size (mm) | | | |
|---|---|---|---|---|
| | 0 days | Day 3 | Day 5 | Day 7 |
| Example 5 | 6.10 | 5.87 | 4.73 | 2.86 |
| Example 6 | 5.95 | 5.86 | 5.03 | 3.93 |
| Example 7-1 | 6.52 | 6.19 | 4.51 | 1.83 |
| Example 7-2 | 6.27 | 5.86 | 4.01 | 0.96 |
| Example 7-3 | 6.05 | 5.35 | 3.26 | 0.73 |

TABLE 5

Comparison of treatment for number of ulcers

| Group | Number of ulcers | | | |
|---|---|---|---|---|
| | 0 days | Day 3 | Day 5 | Day 7 |
| Example 5 | 2.70 | 2.60 | 1.70 | 0.96 |
| Example 6 | 2.50 | 2.50 | 1.80 | 1.32 |
| Example 7-1 | 3.00 | 2.70 | 1.50 | 0.82 |
| Example 7-2 | 2.20 | 1.83 | 0.95 | 0.63 |
| Example 7-3 | 2.40 | 2.05 | 0.70 | 0.32 |

TABLE 6

Comparison of treatment for Pain measurement

| Group | Pain scale | | | |
|---|---|---|---|---|
| | 0 days | Day 3 | Day 5 | Day 7 |
| Example 5 | 8.30 | 8.05 | 5.25 | 3.05 |
| Example 6 | 7.50 | 6.95 | 3.80 | 2.50 |
| Example 7-1 | 7.30 | 6.25 | 3.10 | 1.50 |
| Example 7-2 | 7.80 | 6.03 | 2.05 | 0.96 |
| Example 7-3 | 8.05 | 5.93 | 1.35 | 0.50 |

TABLE 7

Comparison of treatment for erythema levels

| Group | Pain scale | | | |
|---|---|---|---|---|
| | 0 days | Day 3 | Day 5 | Day 7 |
| Example 5 | 2.80 | 2.50 | 1.60 | 0.88 |
| Example 6 | 2.65 | 2.45 | 1.95 | 1.05 |
| Example 7-1 | 2.30 | 2.05 | 1.21 | 0.80 |
| Example 7-2 | 2.50 | 2.25 | 1.02 | 0.52 |
| Example 7-3 | 2.85 | 2.00 | 0.80 | 0.23 |

TABLE 8

Comparison of onset and duration of pain relief

| Group | Onset of pain relief | Duration of pain relief |
|---|---|---|
| Example 5 | 128 second | 2.50 h-3.20 h |
| Example 6 | 90 second | 2.40 h-3.10 h |
| Example 7-1 | 82 second | 3.15 h-3.45 h |
| Example 7-2 | 94 second | 3.20 h-4.30 h |
| Example 7-3 | 100 second | 3.00 h-4.20 h |

The result shows that Examples 7-1 to 7-3 (the present oral patches with two drugs) provided the best results in reducing the size of the ulcer, reducing the pain, and reducing the erythema levels, comparing with the results Examples 5 and 6 (single drug patch).

The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. A bilayer oral patch, comprising:
   (a) a drug layer comprising 3%-20% by weight (w/w) of amorphous tetracaine or a pharmaceutically acceptable salt thereof, 0.1%-2.0% w/w of amorphous triamcinolone or a pharmaceutically acceptable salt thereof, 20-90% w/w of a first film-forming material, 1-12% w/w of an adhesive, and 1-20% w/w of a cooling excipient; and
   (b) a backing layer comprising 70-95% by weight of a second film-forming material and 2-10% by weight of a plasticizer, wherein the backing layer prevents the tetracaine, the triamcinolone, or their pharmaceutically acceptable salts, from diffusing into the oral cavity;
   wherein the first film-forming material comprises (a) hypromellose acetate succinate (HPMCAS) and povidone (PVP), (b) ethyl cellulose and PVP, (c) HPMCAS and polyethylene glycol (PEG), or (d) HPMCAS and hydroxypropyl cellulose (HPC);
   the adhesive is selected from the group consisting of: polyacrylic acid, sodium alginate, copolymer of ethyl acrylate methyl methacrylate, guar gum, sodium carboxyl methyl cellulose, 5-methyl pyrrolidone chitosan, polyglutamic acid, polycarbophil, dextran sulfate, and any combination thereof;
   the cooling excipient is selected from the group consisting of: camphor, menthol, mint oil, clove oil, menthyl acetate, xylitol, sorbitol, thymol, and any combination thereof; and
   the second film-forming material is selected from the group consisting of: HPMC, HPC, hydroxyethyl cellulose (HEC), hydroxypropylated high amylose starch, methylmethacrylate-based copolymer, povidone, collagen, gelatin, pectin, cellulose acetate phthalate (CAP), polyvinyl alcohol (PVA), polyvinyl alcohol phthalate (PVAP), and any combination thereof.

2. The bilayer oral patch according to claim 1, wherein the first film-forming material comprises HPMCAS and PVP.

3. The bilayer oral patch according to claim 1, wherein the second film-forming material is selected from the group consisting of: HPMC, HPC, HEC, hydroxypropylated high amylose starch, methylmethacrylate-based copolymer, povidone, and any combination thereof.

4. The bilayer oral patch according to claim 1, wherein the drug layer further comprises a plasticizer in an amount of 1-12% w/w.

5. The bilayer oral patch according to claim 4, wherein the plasticizer in the drug layer and the plasticizer in the backing layer are independently selected from the group consisting of: glycerin, triethyl citrate, propylene glycol, and any combination thereof.

6. The bilayer oral patch according to claim 1, wherein the thickness of the backing layer is 100-200 μm.

7. The bilayer oral patch according to claim 1, wherein the amount of the tetracaine or its pharmaceutically acceptable salt is 1-6 mg.

8. The bilayer oral patch according to claim 1, wherein the amount of the triamcinolone or its pharmaceutically acceptable salt is 0.03-0.65 mg.

9. The bilayer oral patch according to claim 1, wherein the drug layer further comprises 1-8% w/w of one or more flavoring agents.

10. The bilayer oral patch according to claim 1, wherein the backing layer further comprises 1-8% w/w of one or more flavoring agents.

11. The bilayer oral patch according to claim 1, wherein the drug layer comprises amorphous tetracaine hydrochloride and amorphous triamcinolone acetonide.

12. The bilayer oral patch according claim 11, wherein the drug layer comprises 3%-20% w/w of amorphous tetracaine hydrochloride, 0.1%-2.0% w/w of amorphous triamcinolone acetonide, 30-90% w/w of the first film-forming material, 1-8% w/w of the adhesive, 1-15% w/w of the cooling excipient, and 1-12% w/w of a plasticizer; and
   (b) the backing layer comprises 80%-95% by weight of the second film-forming material and 2-8% by weight of the plasticizer.

13. The bilayer oral patch according claim 1, having a size from 1 cm×1 cm to 2 cm×2 cm.

14. A method for treating mouth ulcer in a subject, comprising the steps of:
   identifying a subject in need thereof, and
   attaching the bilayer oral patch of claim 1 onto the mucosa of the mouth ulcer of the subject.

15. The bilayer oral patch according to claim 1, wherein the first film-forming material comprises ethyl cellulose and PVP.

16. The bilayer oral patch according to claim 1, wherein the first film-forming material comprises HPMCAS and PEG.

17. The bilayer oral patch according to claim 1, wherein the first film-forming material comprises HPMCAS and HPC.

* * * * *